United States Patent [19]

Mabille

[11] Patent Number: 4,830,210
[45] Date of Patent: May 16, 1989

[54] CLOSURE MEANS FOR A BOTTLE FILLED WITH A FLUID

[75] Inventor: Pierre Mabille, Le Sentier, Switzerland

[73] Assignee: EMS Electro Medical Systems S.A., Le Sentier, Switzerland

[21] Appl. No.: 122,076

[22] Filed: Nov. 18, 1987

[30] Foreign Application Priority Data

Nov. 26, 1986 [DE] Fed. Rep. of Germany ....... 3640424
Feb. 11, 1987 [DE] Fed. Rep. of Germany ....... 3704193

[51] Int. Cl.$^4$ ............................................. B65D 83/14
[52] U.S. Cl. ..................................... 215/309; 141/383; 215/313
[58] Field of Search ............... 215/309, 310, 315, 313; 141/383, 384, 325, 326

[56] References Cited

U.S. PATENT DOCUMENTS 3,855,997 12/1974 Sauer .............................. 215/309 X Primary Examiner—Donald F. Norton
Attorney, Agent, or Firm—Ratner & Prestia

[57] ABSTRACT

A closure means for a bottle filled with a fluid comprises at least two closure disks that are each provided with at least one discharge opening at a common off-center position so that only in a singular relatively rotated position of these two disks a discharge of the bottled fluid will be made possible. This relatively rotated position is obtained by means of a fitting which may be fastened to the bottleneck through a turn-lock fastener and which has at least one discharge tube at a corresponding off-center position and interacting with the discharge opening of the one closure disk to rotate the same into the singular relative rotated position in which the discharge tube as well will be axially aligned with the discharge openings of the two closure disks. A third closure disk is preferably provided for presenting with a concentric guiding slot a first working element of a bayonet-type fastener the second working element of which is presented by the head portion of a coordinated discharge tube of a fitting.

15 Claims, 3 Drawing Sheets

CLOSURE MEANS FOR A BOTTLE FILLED WITH A FLUID

FIELD OF THE INVENTION

This invention relates to a closure means for a bottle filled with a fluid.

BACKGROUND ART

A closure means of the general kind as herein referred usually comprises a single closure disk which is secured in any suitable manner to the bottleneck portion of a bottle for closing its opening, the closure disk being provided in its centre with a single discharge opening allowing the bottled fluid to be discharged whenever a separate closure cap that normally covers this closure disk has been removed from the bottle. Many different designs of such closure means are known including also closure disks which at their central discharge opening are provided with an axially extending spout for directing the fluid during its exit from the bottle and also including different principles for the removable attachment of the closure cap to the bottleneck which is usually done by means of a turn-lock fastener in the form of either a screw-type locking fastener comprising an outer thread on the bottleneck and an inner thread on the closure cap or in the form of a bayonet-type fastener that comprises corresponding male and female working elements also on the bottleneck and the closure cap, respectively.

With all of these known closure means the inherent disadvantage must be faced that when the closure cap has been removed it also will be possible to manipulate the bottled fluid in an eventually unallowable manner by filling into the bottle via the then uncovered discharge opening any arbitrary substance which then will falsify the quality of the bottled fluid. When the closure cap is removed the bottled fluid then of course is also directly subjected to an interchange with the atmosphere which could be detrimental for fluids that necessitate a delicate handling such as certain pharmaceutical compositions or which could even be dangerous in case for example of fluids that generate toxic smokes when exposed to the air.

This invention accordingly deals with the object of providing a closure means of the general kind as above referred which guarantees a more safe-proof botteling of a fluid. In particular, an improved closure means for a bottle would be desirable which when used for a dental apparatus operating with air under pressure for the supply of a fluid to a handpiece will allow the dentist to arrange the bottle on the dental apparatus with any suitable fluid connection through its closure means in a simple and correspondingly safe-proof manner to thereby guarantee that only any special fluid filled into such bottles will be used for any particular dental treatment at the time when the bottle has been arranged on the dental apparatus.

SUMMARY OF THE INVENTION

According to the present invention, there is provided a closure means which comprises two closure disks that are each provided with at least one discharge opening at a corresponding off-center position so that only in a single relative rotational position of both closure disks these discharge openings will be mutually aligned for then allowing an exit of the bottled fluid which is not possible with the misaligned arrangement of the discharge openings existing in all other relative rotational positions of the two closure disks. The inventive closure means further comprises a fitting which by means of a turn-lock fastener may be fastened to the bottleneck and which is provided with a discharge tube at a corresponding off-center position so that through an interaction of this tube with the discharge opening of the one closure disk the same will be rotated relative to the second closure disk while the fitting is being fastened to the bottleneck, the relative rotation of both closure disks being thereby controlled in such a manner that when the fitting is fixedly fastened to the bottleneck its discharge tube will be axially aligned with the discharge openings of both closure disks for then allowing an exit of the bottled fluid via the discharge tube.

The present invention accordingly provides a closure means which first necessitates the attachment of a specifically designed fitting to the bottleneck before the bottled fluid may be discharged from the bottle through a discharge tube of the fitting. The bottled fluid is therefore free of any arbitrary manipulation and also free of any interchange with the surrounding atmosphere so that also in accordance with the different inventive embodiments of such a closure means the same will be most useful for bottles that are filled with a fluid necessitating a delicate handling. The inventive closure means is furthermore provided with such a design as to allow therewith a simple and uncomplicated interconnection of the bottle with the fitting when the same is formed as a connecting member of a dental apparatus operating with air under pressure for supplying the bottled fluid then also via a discharge tube of such a member to an interconnected handpiece.

DETAILED DESCRIPTION OF THE INVENTION

Figure 1:
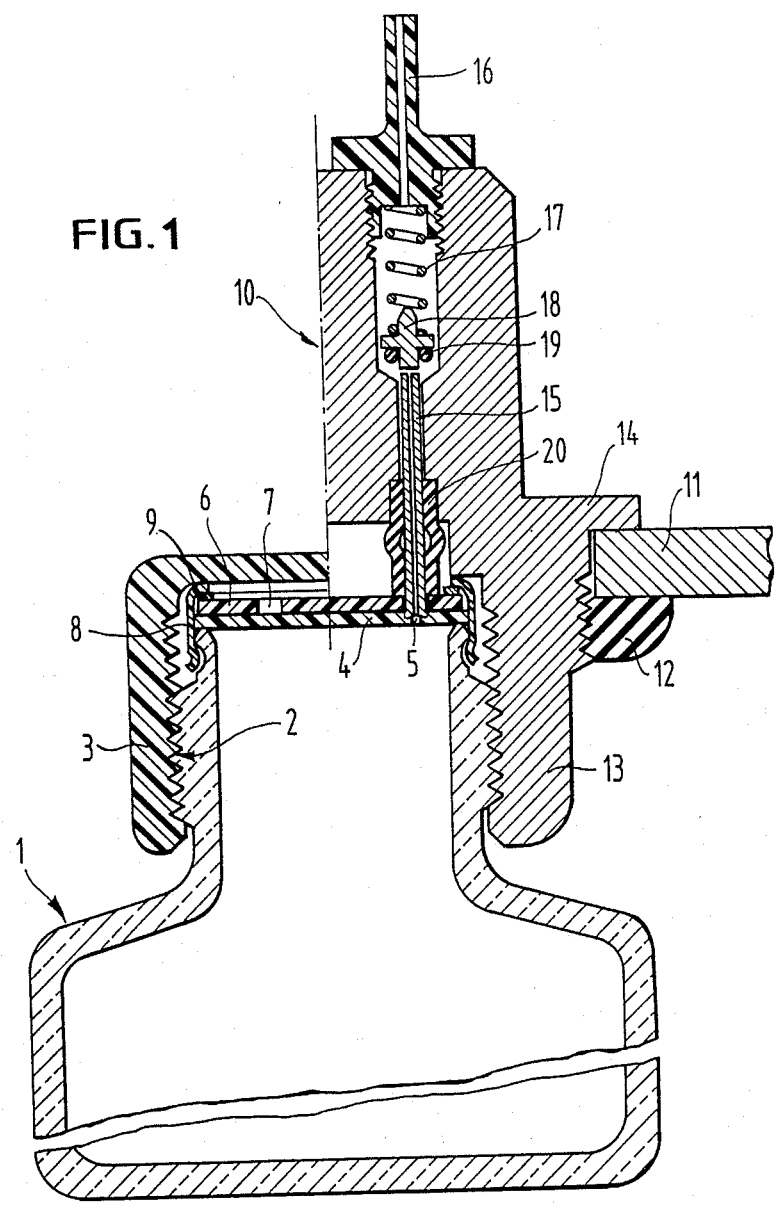
FIG. 1 is a schematic sectional view of a first embodiment of the invention and shows with the left half of the drawing a bottle closed with a screw cap and with its right half the same bottle as fastened to a fitting forming a connecting member of a dental apparatus.
Figure 3:
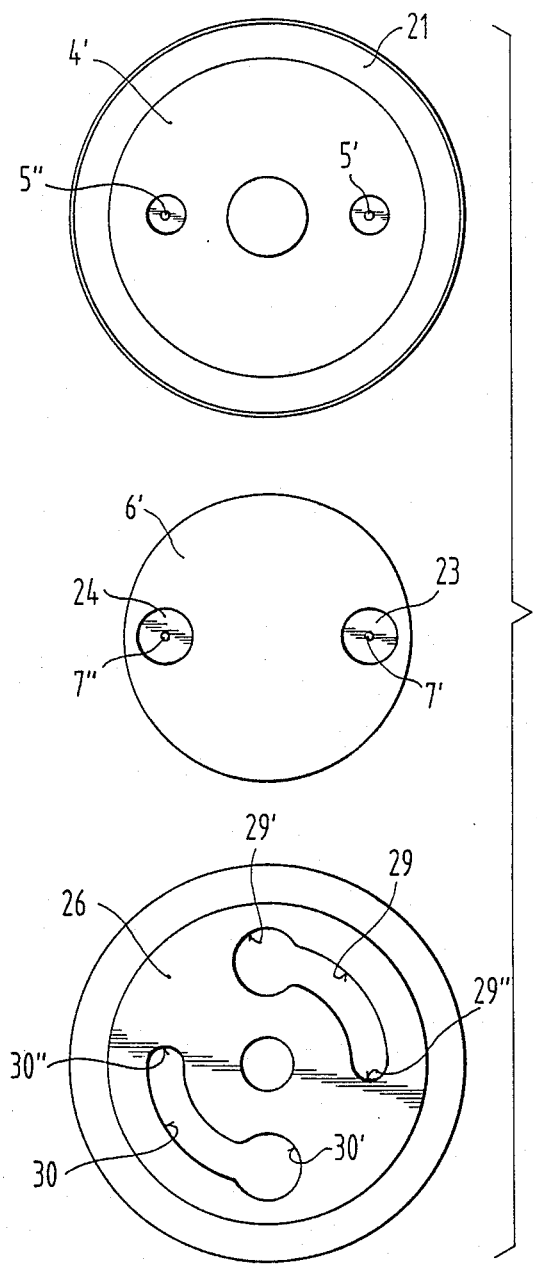
FIG. 3 is a schematic plan view of the three closure disks of the closure means of FIG. 2.

FIG. 1 shows for a first embodiment of the invention a bottle 1 having a bottleneck that is formed with an outer thread of a turn-lock fastener 2 by means of which a closure cap 3 being formed with a corresponding inner thread may be fastened to the bottle for closing its opening. A first closure disk 4 is supported by a rim portion of the bottleneck for covering inside of the closure cap 3 the opening of the bottleneck. The first closure disk 4 is provided with a first off-center discharge opening 5 and also with an angularly offset second discharge opening at the same off-center position. A second closure disk 6 is arranged on top of the first closure disk 4 for normally covering its first and second discharge openings with the exception of a singular relatively rotated position of the two closure disks in which a first off-center discharge opening 7 and a correspondingly provided second off-center discharge opening of this second closure disk will then be arranged directly above the first and second discharge openings of the first closure disk. Although the second off-center discharge openings of the two closure disks 4 and 6 are not shown in FIG. 1 their relative position can be easily derived from the representation in FIG. 3 showing for a second embodiment of the invention two corresponding first and second closure disks 4' and 6' being each provided with a first off-center discharge opening 5' and 7', respectively, and also with an angularly offset second discharge opening 5" and 7", respectively, at the same off-center position and conveniently at a diametrically opposite location relative to the respectively coordinated first discharge opening. Both closure disks 4 and 6 are further held on the bottleneck by a clamp member 8 which on top of the second closure disk 6 is underlaid with a washer 9 so that when the closure cap 3 has been removed from the bottleneck the two closure disks may be easily rotated relative to each other.

The right half of FIG. 1 shows a fitting 10 which forms a connection member of a dental apparatus that operates with air under pressure for supplying a bottled fluid to a dental handpiece. The dental apparatus could be of the kind as for example described in U.S. Pat. Nos. 3,227,158 and 3,863,628 each comprising a motor-pump assembly for producing the supply pressure for a fluid to be supplied to a handpiece. The fitting 10 accordingly is shown as being fixed to a housing 11 of such a dental apparatus and having an outwardly projecting tubular portion 13 that is formed with an inner thread corresponding to the inner thread of the closure cap 3 so that when the same has been removed the bottle 1 may be fastened with the outer thread of its bottleneck to this tubular portion 13 of the fitting 10 by means accordingly of an identical turn-lock fastener. The tubular portion 13 projects through an opening of the housing 11 which is sealed by an outer screw nut 12 and an inner circular flange 14 of the fitting.

The inner portion of the fitting 10 is formed with two bores at the same off-center position and with the same angular offset as the first and second discharge openings of the first and second closure disks. Each bore is provided at its one end portion with an axially movable discharge tube 15 and at its opposite end portion with a nipple 16 on which a spring 17 is supported that biases the coordinated discharge tube 15 in an outward direction. The outwardly projecting ends of both discharge tubes 15 which are each axially guided by a flexible bearing bush 20 may therefore be pressed inwardly against the biasing force of the coordinated spring 17 which only for the one discharge tube forms at the same time a structural component of a non-return valve the valve body 18 of which may be seated on the inner end of the coordinated discharge tube 15 in a fluid-tight manner as obtained by an O-ring 19 of this valve body. When the valve body 18 is seated on the inner end of its coordinated discharge tube 15 the outer end of the same will slightly project over the face of its coordinated bearing bush 20 as long as there exists no contact with the second closure disk 6 during the fastening of the bottle on the tubular portion 13 of the fitting 10. The same slightly outwardly projecting arrangement then also exists at the second discharge tube where no corresponding non-return valve is provided and the coordinated spring therefore directly acts on the inner end of the discharge tube.

With the closure cap 8 removed no exit of the bottled fluid will be allowed as long as the first and second discharge openings of the second closure disk 6 are not aligned with the corresponding first and second discharge openings of the underlaying first closure disk 4. When the bottle 1 is rotatively united at its bottleneck with the tubular portion 13 of the fitting 10, the outer ends of both discharge tubes 15 will eventually be brought into contact with the second closure disk 6 and since both discharge tubes are biased outwardly they eventually will also be forced to drop into the first and second discharge openings of the second closure disk. With a continuous rotation of the bottle, the second closure disk 6 will then be caused to rotate relative to the first closure disk 4 until a singular relatively rotated position has been obtained in which both discharge tubes 15 are forced to then also drop into the first and second discharge openings of the first closure disk. For then avoiding any otherwise possible pressing of both discharge tubes through the first and second discharge openings of the first closure disk 4 these discharge openings are each conveniently provided with a stepped hole the larger diameter of which corresponds with the diameter of the discharge tubes the advance of which will then automatically be stopped with the inner shoulder of such stepped bores. With a still continued rotation of the bottle, both closure disks will then be commonly arrested through the interaction with the two discharge tubes which accordingly retain their axial alignment with the first and second discharge openings of the first and second closure disks until the moment when the bottle is fixedly united with the tubular portion 13 of the fitting. Since during this final rotation the non-return valve will be opened by an unseating of its valve body 18 against the force of its spring 17 as shown in FIG. 1, the bottled fluid may then be supplied via this opened valve to a handpiece of the dental apparatus via a flexible hose that will be connected to the coordinated nipple 16, the discharge of the bottled fluid being started by the admission of air under pressure via the other discharge tube the coordinated nipple of which is connected to a pressure source also by means of a flexible hose. When this discharge of the bottled fluid takes place, a fluid-tight sealing will be secured by the flexible bearing bush 20 which receives the deformation shown in the drawing during the final rotation of the bottle and therefore more or less concurrently with the unseating of the valve body 18 of the non-return valve.

When the bottle 1 is unscrewed from the tubular portion 13 of the fitting 10, the two discharge tubes 15 will then be retracted first from the openings of the first closure disk 4 and subsequently from the openings of the second closure disk 6. When the second closure disk 6 has a thickness that is larger than at least twice the value of the pitch of the screw-type locking fastener, the retraction of the two discharge tubes 15 from the two openings of the second closure disk 6 will automatically be finished in a relatively rotated position of this second closure disk in which its openings will not be aligned with the openings of the first closure disk 4 so that these openings are then covered by the second closure disk.

Figure 2:
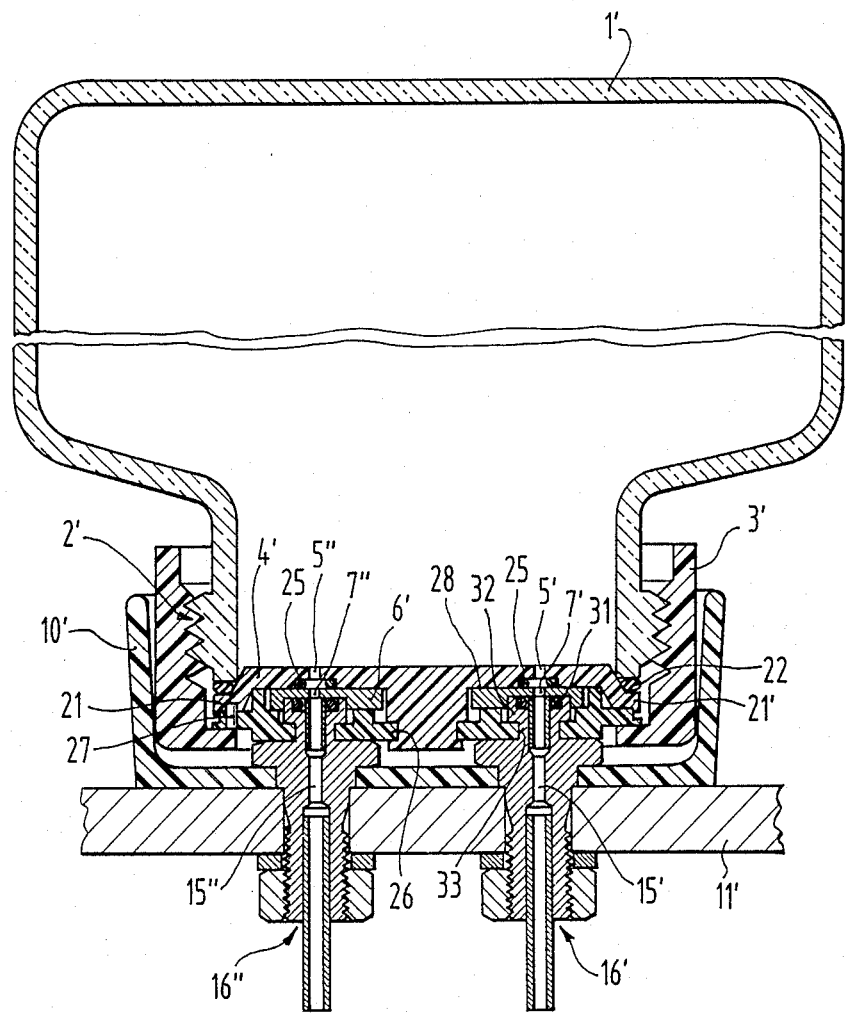
FIG. 2 is a schematic sectional view of a second embodiment of the invention and shows a bottle that is connected through its closure means to a fitting forming a connecting member of a dental apparatus.

In the above described first embodiment of the invention, the screw-type locking fastener 2 could be replaced by a bayonet-type fastener which then would comprise as well corresponding male and female working elements on the bottleneck and on the closure cap 3 as well as on the tubular portion 13 of the fitting, respectively. With such a bayonet-type fastener it no longer would be necessary to arrange the discharge tubes 15 in an axially movable manner since thereby the singular relatively rotated position of the first and second closure disks in which the discharge tubes are axially aligned with the discharge openings of these disks will automatically be obtained while the bottle is rotatively united with the fitting. In FIG. 2 a second embodiment of the invention is shown which principally corresponds with the first embodiment so that all corresponding components are referred to with the same numerals supplemented with a prime notation. For this second embodiment the bottle 1' is shown upside down which would be the normal position for its preferred use with a dental apparatus on the housing 11' of which a corresponding fitting 10' would be arranged which again forms a fitting by means of which a forced discharge of the bottled fluid is made possible. The fitting 10' is of such a design as to allow an interconnection with the closure means of the bottle 1' even with a corresponding closure cap 3' remaining fastened to the bottleneck again by means of a turn-lock fastener 2' which instead of the shown screw-type locking fastener could also be formed as a bayonet-type fastener.

The closure means comprises a first closure disk 4' having the two off-center discharge openings 5' and 5" and a second closure disk 6' with the corresponding two offcenter discharge openings 7' and 7" as already referred to. The first closure disk 4' has a circular flange 21 for its centering in the opening of the bottleneck and for centering on the other side the second closure disk 6' so that the same may be precisely rotated relative to the first closure disk over a quarter turn back and forth for aligning and misaligning the pairs of first and second discharge openings 5',7' and 5",7", respectively, of the first and second closure disks.

For this second embodiment of the invention the closure means is further complemented by a third closure disk 26 which is arranged on top of the second closure disk 6' and supported by the circular flange 21 of the first closure disk 4' in such a manner that with a fast connection of these first and third closure disks as obtained by a pin 27 or in any other suitable manner the second closure disk 6' can be freely rotated in the space provided between these two disks. The thickness of the second closure disk 6' should conveniently be less than the height of this space between the first and third closure disks so that the second closure disk 6' may be biased outwardly by two O-rings 25 which are provided for sealing the fluid connection between the pairs of first and second discharge openings at the interface 28 of the first and second closure disks. The third closure disk 26 is as well centered by the circular flange 21 of the first closure disk 4' actually in such a manner that by this centering the second closure disk 6' receives its centering also relative to the third closure disk. The third closure disk 26 is provided with two guiding slots 29 and 30 which each extend over a quarter of a circular line having a radius that corresponds with the off-center position of the pairs of first and second discharge openings of the first and second closure disks. Each guiding slot is at its one end provided with an enlarged through opening 29' and 30', respectively, the diameter of which corresponds to the diameter of two recesses 23 and 24 that are formed in the second closure disk 6' concentric with the first and second discharge openings 7',7" of the same. This diameter further corresponds with the diameter of a head portion 32 of two discharge tubes 15' and 15" which form as in the first embodiment two corresponding components of the fitting 10' for allowing via a corresponding nipple 16' a supply of the bottled fluid to a handpiece whenever air under pressure is supplied via the nipple 16" of the second discharge tube 15" to the inside of the bottle 1'. As will be described in more detail, the head portions 32 of these first and second discharge tubes form a first working element of a bayonet-type fastener in that each head portion is provided with an undercut circular groove 33 the width of which corresponds with the thickness of the third closure disk 26 and the core diameter of which corresponds with the width of each of the two guiding slots 29,30 which accordingly form a second working element of this bayonet-type fastener for which the second end 29" and 30", respectively, of the guiding slots forms a stopping means for the interacting head portions 32 for limiting the rotation of the second closure disk 6' relative to the first and third closure disks. In this stop position the two discharge tube 15',15" are axially aligned with the two pairs of first and second discharge openings 5',7' and 5",7", respectively, of the first and second closure disks 4' and 6' as shown in FIG. 2 so that thereby also for this second embodiment of the invention a singular relatively rotated position of the second closure disk 6' relative to the interconnected first and third closure disks 4' and 26 is presented which contrary to all other relatively rotated positions of the three closure disks singularly allows a discharge of the bottled fluid. The three closure disks are secured to the bottleneck by means of the closure cap 3' which different from the first embodiment is provided with a central opening so that with the edge portion of the same a corresponding edge portion of the third closure disk 26 may be overlapped for pressing a rim portion 21' of the supporting flange 21 of the first closure disk 4' together with an underlaid sealing ring 22 against the rim of the bottleneck.

Although the operation of the second embodiment of the invention should be clear from this detailed description it may be summarized as follows. With the bottle 1' detached from the fitting 10' no discharge of the bottled fluid will be possible since then the first and second discharge openings 7',7" of the second closure disk 6' are located in a position which is a quarter turn further from the position which is represented in FIG. 3. The corresponding first and second discharge openings 5', 5" of the first closure disk 4' will therefore be covered by the second closure disk 6' and the circular recesses 23 and 24 of the same will be axially aligned with the through openings 29',30' of the two guiding slots 29,30 of the third closure disk 26. These different relatively rotated positions of the three closure disks are secured on the bottleneck by means of the closure cap 3' over which another slip-on cap could be arranged for storage purposes of the bottle. For interconnecting fast the bottle 1' with the two discharge tubes 15',15" of the fitting 10' it only will be necessary to insert their head portions 32 into the through openings 29',30' of the two guiding slots 29,30 of the third closure disk 26 and further into the recesses 23,24 of the second closure disk 6' whereupon with a quarter turn of the bottle 1' in the clockwise direction this second closure disk will be rotated relative to the first and third closure disks 4' and 26 to the position which is shown in FIG. 3. In this relatively rotated position a discharge of the bottled fluid will be made possible as above described whereby with an O-ring 31 provided on the face of the head portions 32 of the two discharge tubes 15',15" a similar fluid-tight intereconnection is presented in respect to the first and second discharge openings of the second closure disk as is presented with the O-rings 25 in respect to the first and second discharge openings of the innermost first closure disk.

While the invention has been shown and described in its preferred embodiments, it will be clear to those skilled in the art to which it pertains, that many changes and modifications may be made thereto without departing form the scope of the invention. The closure means thusly could also be provided with only a single off-center discharge opening in the first and second closure disk and then correspondingly only with a single guiding slot in the third closure disk and a single discharge tube of the fitting whereby such an embodiment could be used in a respectively more safe-proof manner for the same purposes as the closure means so far known in the art are being used. Instead of the pin connection between the first and the third closure disks of the second embodiment these two disks could as well be welded or soldered. Finally there is also no specific limitation in the choice of the material for the different components.

What is claimed is:

1. A closure means for a bottle filled with a fluid, comprising:
    a first closure disk covering an opening of a bottleneck, said first closure disk having at least one off-center discharge opening for the fluid;
    a second closure disk arranged on top of the first closure disk for normally covering the discharge opening, said second closure disk having at least one discharge opening at the same off-center position as the discharge opening of said first closure disk;
    a fitting, removably connected to said bottleneck, said fitting having at least one off-center discharge tube that interacts with the discharge opening of said second closure disk for rotating the same relative to the said first closure disk while the bottle is rotatively united with said fitting to obtain a singular relatively rotated position of said first and second closure disks in which said discharge tube is axially aligned with the discharge openings for allowing an exit of the bottled fluid via said discharge tube;
    a turn-lock fastener for attaching the fitting to the bottleneck;
    said turn-lock fastener being formed either as a screw-type locking fastener or as a bayonet-type fastener for connecting the fitting to the bottleneck in the same manner as a closure cap may be connected to said bottle-neck instead of said firing fitting to normally cover both of said first and second closure disks for preventing any discharge of the fluid.

2. A closure means according to claim 1 wherein said first discharge tube is provided with a check valve that opens in the exit direction of the fluid.

3. A closure means according to claim 1 wherein said second closure disk has a thickness that is larger than at least twice the value of the pitch of said screw-type locking fastener.

4. A closure means according to claim 1 wherein each closure disk is formed with a second discharge opening at the same off-center position and with such a common angular offset with respect to its coordinated first discharge opening that in said singular relatively rotated position of said first and second closure disks the second discharge openings are arranged one above the other.

5. A closure means according to claim 4 wherein a second off-center discharge tube of the fitting is axially aligned with said second discharge openings in said singular relatively rotated position of said first and second closure disks.

6. A closure means for a bottle filled with a fluid, comprising:
    a first closure disk covering an opening of a bottleneck, said first closure disk having at least one off-center discharge opening for the fluid;
    a second closure disk arranged on top of said first closure disk for normally covering the discharge opening, said second closure disk having at least one discharge opening at the same off-center position as the discharge opening of said first closure disk;
    a fitting, removably connected to said bottleneck, said fitting having at least one off-center discharge tube that interacts with the discharge opening of said second closure disk for rotating the same relative to said first closure disk while the bottle is rotatively united with said fitting for obtaining a singular relatively rotated position of said first and second closure disks in which said discharge tube is axially aligned with the discharge openings for allowing an exit of the bottled fluid via said discharge tube;
    a third closure disk arranged on top of said second closure disk said third closure disk having at an off-center position corresponding to the off-center position of the discharge openings, a guiding slot of such length that when said second closure disk is being rotated by said discharge tube relative both to said first closure disk and to said third closure disk said singular relatively rotated position is obtained with a stop position of said discharge tube at the end of said guiding slot; and
    a bayonet-type fastener for rotatably attaching the fitting to the bottleneck through the cooperation between said discharge tube and said guiding slot.

7. A closure means according to claim 6 wherein said third closure disk is non-rotatably interconnected with said first closure disk, said first discharge tube having a head portion which is provided with an undercut circular groove the width of which corresponds with the thickness of said third closure disk and the core diameter of which corresponds with the width of said guiding slot which at its one end is provided with a through-hole having the large diameter of said head portion of said first discharge tube.

8. A closure means according to claim 6 wherein said third closure disk is supported by a circular flange at an edge portion of said first closure disk which flange centers said second closure disk having a thickness that is somewhat smaller than the supporting height of said third closure disk.

9. A closure means according to claim 6 wherein said first, second and third closure disks are supported by a rim of the bottleneck portion and are fastened to the same by means of a closure cap which has a bottom opening for overlapping with its edge portion a corresponding edge portion of said third closure disk.

10. A closure means according to claim 6 wherein said first, second and third closure disks are centered in the bottle opening means of said circular flange of said first closure disk.

11. A closure means according to claim 6 wherein O-rings are providing for obtaining a mutually fluid-tight interconnection between said first discharge tube and said first discharge openings in said singular relatively rotated position of said first, second and third closure disks.

12. A closure means according to claim 6 wherein each closure disk is formed with a second discharge opening at the same off-center position and with such a common angular offset with respect to its coordinated first discharge opening that in said singular relatively rotated position of said first and second closure disks the second discharge openings are arranged one above the other.

13. A closure means according to claim 12 wherein a second off-center discharge tube of the fitting is axially aligned with said second discharge openings in said singular relatively rotated position of said first and second closure disks.

14. In a dental apparatus for supplying fluid from a bottle to a dental handpiece, under either positive or negative pressure, the improvement comprising the closure means of claim 6.

15. In dental apparatus for supplying fluid from a bottle to a dental handpiece, under either positive or negative pressure, the improvement comprising the closure means of claim 1.

* * * * *